United States Patent
Foehrenbach

(10) Patent No.: US 9,554,965 B2
(45) Date of Patent: Jan. 31, 2017

(54) DEVICE FOR INTRODUCING SHOCK WAVES INTO A LIVING BODY AND USE THEREOF

(75) Inventor: Marianne Foehrenbach, Doeggingen (DE)

(73) Assignee: Ferton Holding SA, Delemont (CH)

( * ) Notice: Subject to any disclaimer, the term of this patent is extended or adjusted under 35 U.S.C. 154(b) by 150 days.

(21) Appl. No.: 13/124,299

(22) PCT Filed: Oct. 12, 2009

(86) PCT No.: PCT/EP2009/007322
§ 371 (c)(1),
(2), (4) Date: Jun. 21, 2011

(87) PCT Pub. No.: WO2010/043360
PCT Pub. Date: Apr. 22, 2010

(65) Prior Publication Data
US 2011/0245736 A1    Oct. 6, 2011

(30) Foreign Application Priority Data
Oct. 14, 2008  (DE) .................. 10 2008 051 174
Sep. 22, 2009  (DE) .................. 10 2009 042 276

(51) Int. Cl.
| | |
|---|---|
| A61H 1/00 | (2006.01) |
| A61H 23/00 | (2006.01) |
| A61B 17/22 | (2006.01) |
| A61H 23/04 | (2006.01) |
| A61B 17/92 | (2006.01) |

(52) U.S. Cl.
CPC ....... *A61H 23/008* (2013.01); *A61B 17/22012* (2013.01); *A61H 23/04* (2013.01); *A61B 2017/925* (2013.01); *A61H 2201/10* (2013.01); *A61H 2201/1246* (2013.01); *A61H 2201/1685* (2013.01)

(58) Field of Classification Search
CPC ............................. A61B 17/2251; G10K 15/06
USPC ............................................................ 601/4
See application file for complete search history.

(56) References Cited

U.S. PATENT DOCUMENTS

| | | | |
|---|---|---|---|
| 1,599,628 A | 9/1926 | Ahlgren | |
| 1,657,765 A * | 1/1928 | Pasque | ......................... 601/108 |
| 1,796,444 A | 3/1931 | Dell'era et al. | |
| 3,840,992 A * | 10/1974 | English | ........................... 433/89 |
| 4,088,128 A * | 5/1978 | Mabuchi | ....................... 601/101 |
| 4,549,535 A | 10/1985 | Wing | |
| 4,566,442 A | 1/1986 | Mabuchi et al. | |
| 5,160,336 A * | 11/1992 | Favre | ........................... 606/128 |

(Continued)

FOREIGN PATENT DOCUMENTS

| | | |
|---|---|---|
| DE | 3315185 | 11/1983 |
| DE | 19725477 | 12/1998 |

(Continued)

*Primary Examiner* — Tse Chen
*Assistant Examiner* — Hien Nguyen
(74) *Attorney, Agent, or Firm* — Bachman & LaPointe, PC

(57) ABSTRACT

In a device for introducing shock waves into a living body by way of at least one element (4; 12; 14) which transmits the shock waves and upon which shock pulses act, wherein at least one spring member (2) is used for generating the shock waves, a tensioning device is associated with the spring member and allows for an abrupt release of the spring member while delivering a shock pulse.

16 Claims, 2 Drawing Sheets

(56) References Cited

U.S. PATENT DOCUMENTS

| | | | |
|---|---|---|---|
| 5,176,688 A | 1/1993 | Narayan et al. | |
| 5,868,756 A | 2/1999 | Henry et al. | |
| 5,906,623 A | 5/1999 | Peterson | |
| 6,413,230 B1 * | 7/2002 | Haupt et al. | 601/2 |
| 7,470,274 B2 | 12/2008 | Lebet | |
| 2006/0155210 A1 * | 7/2006 | Beckman et al. | 600/567 |
| 2008/0167661 A1 | 7/2008 | Pardoll et al. | |
| 2009/0118741 A1 | 5/2009 | Lebet | |
| 2009/0259193 A1 * | 10/2009 | Chen | 604/192 |

FOREIGN PATENT DOCUMENTS

| | | |
|---|---|---|
| DE | 202006007044 | 9/2006 |
| FR | 2851153 | 8/2004 |

\* cited by examiner

DEVICE FOR INTRODUCING SHOCK WAVES INTO A LIVING BODY AND USE THEREOF

BACKGROUND OF THE INVENTION

The invention relates to an apparatus for introducing shock waves into a living body via at least one element which transmits the shock waves and on which shock pulses act, at least one spring member serving to generate the shock pulses. The apparatus is preferably designed as a medical handheld appliance which can be used both in intracorporeal shock wave lithotripsy and in extracorporeal shock wave orthopedics as part of the disintegration of calculi or superficially in the case of diseased parts of the body.

A device of this kind is generally known for example from U.S. Pat. No. 4,549,535 for the treatment of humans. Since it has a soft tip, it cannot be used for lithotripsy.

The disintegration of concretions in vivo by the use of shock waves (lithotripsy) is already used successfully in modern medicine. The concretions, such as kidney stones, are disintegrated in the body of a human into small fragments, which are then intended to be excreted from the body via the urinary tract.

In the present case, a shock wave is understood to mean in particular any compression wave generated by an impact.

The prior art describes various apparatuses and methods for generating shock waves for disintegrating concretions in a living body. Thus, the U.S. Pat. No. 5,868,756 describes a handheld appliance for use in intracorporeal shock wave lithotripsy, said appliance having a probe which serves as a waveguide for transmitting shock waves and is dimensioned in an appropriate manner for introduction into an endoscope.

The shock energy for generating the shock waves is obtained in this handheld appliance by a projectile or percussion part that can move back and forth pneumatically in a guide tube, specifically in that it periodically strikes an appropriately large mass part which then transfers the impact force acting on its target area to the probe adjoining the mass part.

This US document also states that instead of a pneumatic drive for the percussion part, a hydraulic or electromagnetic drive can alternatively be realized.

Furthermore, DE 197 25 477 C2 describes a medical instrument in the form of a handheld appliance for treating biological tissue (orthopedics), said medical instrument being intended to generate extracorporeal pressure waves. These pressure waves are intended to be introduced into the body of living beings with the aid of a transmitting element. To this end, the transmitting element has a blunt probe tip having a flat output interface, by way of which unfocussed, mechanically generated pressure waves can then be coupled into the biological tissue.

In this instrument, the pressure wave itself is generated by a percussion part that is accelerated pneumatically to a speed of more than 5 m/s and impinges on the transmitting element, it being intended that the probe tip execute a stroke of less than 1 mm. With this handheld appliance, it is further intended that the energy of the pressure waves be distributed evenly over a large region of action, such as an entire region of inflammation, for example.

For example, U.S. Pat. No. 1,796,444 discloses an apparatus for treating the human body with shock waves. In order to generate the shock waves, a spring element is tensioned and then abruptly released. The tensioning device for the spring element is a drive. Disadvantageously, a sudden, abrupt triggering is not possible therewith, since the spring element remains connected to the tensioning device the whole time.

However, the known handheld appliances all have pressure or shock wave generators, and have relatively complicated designs since a compressor, control unit and handpiece are required.

It is an object of the invention to provide an apparatus for introducing or applying shock waves into or onto a living body, the shock wave generator of which has a simple structure and also delivers an exact "hard" impact force. Furthermore, the apparatus should be low-maintenance and be highly suitable for intra- and for extracorporeal treatment, preferably of the human body.

SUMMARY OF THE INVENTION

The foregoing object is achieved according to the invention in a simple manner in the case of an apparatus for introducing shock waves into a living body by the features described hereinbelow.

A tensioning device is assigned to the spring member and enables the spring member to be triggered abruptly, emitting a shock pulse.

By means of a shock wave generator which is designed in this way, it is advantageously possible that the probe transmitting shock waves can be acted on periodically with relatively high ("hard") impact energy, specifically in a similar manner to the firing rate of a machine gun, for which reason the subject matter of the invention can also be called a lithogun or orthogun. The "hard" impact force is achieved primarily by a low-mass element having a high impact velocity.

According to the present invention, it is expedient that preferably a pneumatic or cylindrical mechanical compression spring serves as the spring member and is connected to a percussion part such that it emits the spring force of the compression spring, when its compressive stress is released suddenly, to the transmitting element in the form of a shock pulse.

In this case, the percussion part can be formed as a piston which is guided in a housing part and has a head part that emits the shock pulses and an adjoining cylindrical hollow part. The cylindrical compression spring, which generates the spring forces, is guided at least partially in the hollow part, it being expedient in this case that the compression spring is supported at one end on the rear side of the head part of the piston and at the other end on a housing part of the apparatus.

In a further preferred exemplary embodiment, the apparatus for emitting a shock pulse to the transmitting element should take place pneumatically. To this end, the apparatus preferably comprises a projectile.

Preferably, the apparatus for emitting a shock pulse also comprises a device for subjecting the projectile to the action of compressed air. In a particularly preferred embodiment, said device comprises a piston which is guided in a cylinder. As a result, when the piston has a larger cross section than the projectile, an even greater pressure, depending on the cross-sectional area ratio selected, can advantageously be applied to the projectile.

The cylinder is advantageously connected via a flexible tube to a channel in which the projectile is located. In this channel, the projectile can accelerate until is strikes the transmitting element.

The channel for guiding the projectile can be provided in a barrel having a housing. Set-down surfaces, feet or a suspension apparatus can be integrally formed on the housing.

The piston is accelerated preferably by means of spring force. To this end, the piston is likewise assigned a spring member. The piston advantageously has a rib as a guide for the spring member.

In order to tension and release the spring guided in the percussion part or in the rib of the piston in order to subject the projectile to the action of compressed air, it is advantageous when the piston of the percussion part has along its outer casing at least one rack, into which a pinion engages, said pinion having a toothed ring only on part of its circumference, e.g. over 180° of its circumference, a worm also being possible instead of the pinion. Instead of a separate rack, a toothing formation can also be formed directly in the outer casing of the percussion part.

If the pinion is now rotated, the percussion part moves away from the probe as soon as the partial toothed ring is in engagement with the rack, and the spring guided in the piston of said percussion part is compressed. As soon as the toothed ring of the pinion leaves the rack, that is to say comes out of engagement, the compressed spring can abruptly release its tension and the spring force released thereby accelerates a projectile to the desired speed. This projectile strikes a probe, and generates a shock wave in the applicator, which for its part transfers a corresponding shock wave to the object to be treated.

The respective rotations of the pinion expediently take place by motor, and here by means of a battery-powered electric motor, upstream of which is preferably connected a reduction gear in order to reach suitable rotational speeds of the pinion, which influence the respective impact frequencies.

However, the context of the invention should not include only the arrangement just described, but rather any conceivable retaining apparatus which retains the tensioned compression spring and then releases it in a triggered manner.

When use is made of the apparatus according to the invention for intracorporeal shock wave lithotripsy, it is expedient that here the element that transmits the shock waves is designed in the manner of a probe, in order that it can be introduced into an endoscope, specifically for disintegrating concretions such as kidney stones or gall stones in a living body.

By contrast, when use is made of the apparatus according to the invention for extracorporeal shock wave orthopedics, dermatology and esthetics (cellulite), it is expedient that the element thereof that transmits the shock waves is formed as a rounded spherical segment for applying to the living body. Although this apparatus is suitable also for disintegrating concretions from outside, it is possible to use it to treat above all diseased parts of the body of a human or in animals, in particular in the regions of the tendons, ligaments, bones and the skin (cellulitis, wounds), with shock waves.

In order to handle the apparatus according to the invention properly, it is expedient that it is formed as a medical handheld appliance, i.e. this handheld appliance should only have a size, as seen from its external dimensions, which allows the appliance to be held properly in an adult hand.

This apparatus which is formed as a medical handheld appliance can, in addition to a housing for accommodating the shock wave generator, also advantageously be provided such that optionally an attachment having a probe for lithotripsy or one for orthopedics can be releasably attached to the housing thereof. With such a modular system, the number of types is advantageously reduced, thereby increasing the cost-effectiveness of such a handheld appliance.

BRIEF DESCRIPTION OF THE DRAWINGS

Further features and advantages of the present invention are given in the following description of preferred exemplary embodiments in conjunction with the drawing, in which.

DETAILED DESCRIPTION

Figure 1:
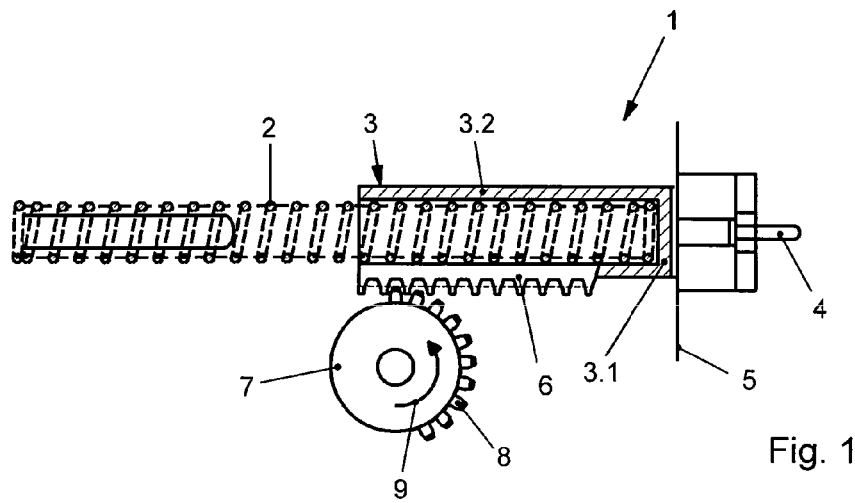
FIG. 1 shows the principle of a shock wave generator according to the invention.

The principle of a shock wave generator 1 illustrated schematically in FIG. 1 has, in order to generate shock pulses, a spring member 2 in the form of a cylindrical compression spring, which is operatively connected to a percussion part 3 which in turn transfers the shock pulses generated to an element 4 that transmits shock waves. The compression spring 2 consists of spring steel, but other materials, such as plastic for example, can also be used.

Figure 2:
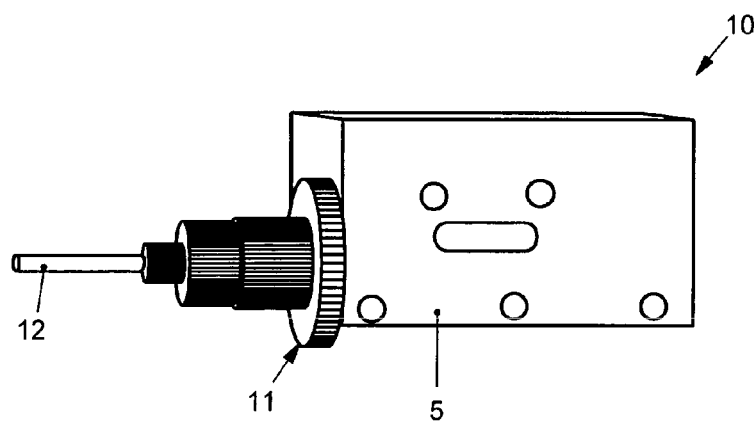
FIG. 2 shows a perspective view of a medical handheld appliance, which is equipped with a shock wave generator according to FIG. 1 and is suitable for intracorporeal shock wave lithotripsy.

The percussion part 3, which is suitably guided in a housing 5 of the apparatus illustrated in FIG. 2, consists of a type of piston having a head part 3.1 that emits the shock pulses and a cylindrical hollow part 3.2 adjoining said head part 3.1.

The compression spring 2 is partially guided in the hollow part 3.2 and is supported at its right-hand end on the rear side of the head part 3.1 and at its left-hand end on a portion (not illustrated in more detail) of the housing 5. The percussion part 3 itself is arranged coaxially with respect to the element 4 that transmits the shock waves.

Furthermore, the hollow part 3.2 of the percussion part 3 has along its outer casing an integral toothing formation or an attached rack 6, into which a pinion 7 or a worm (not illustrated) can be engaged periodically. The pinion 7 has to this end a toothed ring 8 on only a part of its circumference, the profile of said toothed ring 8 corresponding to the profile of the rack 6. In the present exemplary embodiment, the partial toothed ring 8 is limited to a circumferential range of 180°; this is preferred, but it can also be larger or smaller.

The pinion 7 itself is driven via a battery-powered electric motor—indicated by the arrow 9 in FIG. 1—located in the housing 5, a suitable reduction gear being connected upstream of said motor.

The medical handheld appliance—designated 10—illustrated in simplified form in FIG. 2 is in the present case set up for use in intracorporeal shock wave lithotripsy. To this end, there is provided a releasable attachment 11, the element of which—designated 12—that transmits shock waves is designed in the form of a probe. Therefore, this element 12 can be introduced into an endoscope and the distal end of the probe is thus available for disintegrating calculi by means of shock waves transmitted via the probe.

Figure 3:
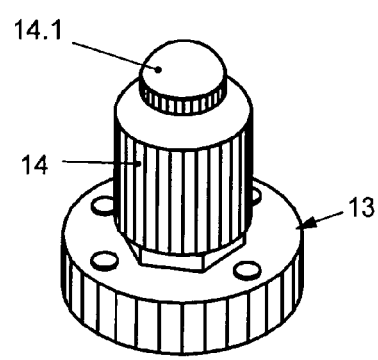
FIG. 3 shows a perspective view on an enlarged scale of a possible interchangeable attachment for the appliance according to FIG. 2, for use in extracorporeal shock wave orthopedics.

In the event that the handheld appliance 10 according to FIG. 2 is intended to be used for extracorporeal shock wave orthopedics, the attachment 11 can also be exchanged for an attachment 13 (FIG. 3), the element of which—designated 14—that transmits shock waves has at its contact region a kind of rounded spherical segment 14.1 that is suitable for external application to a part of the body of a human or animal. Both attachments 11 and 13 are suitable for disintegrating concretions such as kidney stones, urinary stones or gall stones, the attachment 13 in particular being more suitable for subjecting diseased areas of the body, such as tendon or ligament regions, bone parts, areas of skin or simply wounds, to shock waves.

The medical handheld appliance 10 has a size which allows it to be held comfortably by an adult user in their hand.

The present invention functions as follows:

The shock wave generator 1, which is accommodated in the housing 5, is driven counterclockwise at approximately 5 Hz (300 rpm) by an electric motor via a reduction gear (symbolically arrow 9), as a result of which the toothed ring 8 engages periodically in the rack 6 and the percussion part 3 moves to the left by the length of the rack 6, thereby compressing the compression spring 2 by this amount. The impact energy being stored in the compression spring 2 in the process is then released suddenly, i.e. abruptly, specifically as soon as the last tooth of the toothed ring 8 leaves the rack 6. By way of this spring force, which is available on account of the brief release of tension in the compression spring 2, the element 4 or 12 or 14 is acted on abruptly, it being possible also to provide a mass part as it were as a buffer between the end portions of these elements and the head part 3.1.

On account of the abrupt impact of the head part 3.1 against the respective element 4 or 12 or 14, shock waves are produced in the latter and are then used either to disintegrate calculi or else, for example, to break down calcifications in particular areas of the body, such as in areas of the shoulder. How often this impact should take place per second depends in turn on the rotational speed of the pinion 7 and this in turn depends on the desired intensity of the respective treatment.

Figure 4:
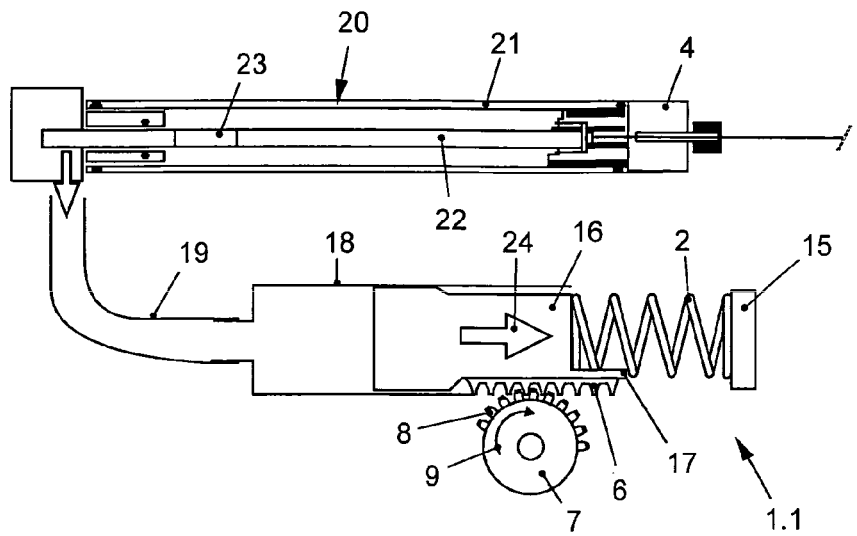
FIGS. 4 to 6 show the principle of a further exemplary embodiment of the shock wave generator according to the invention.
Figure 5:
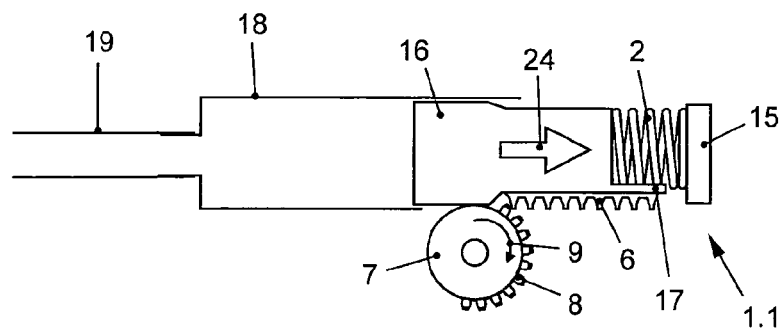
Figure 6:
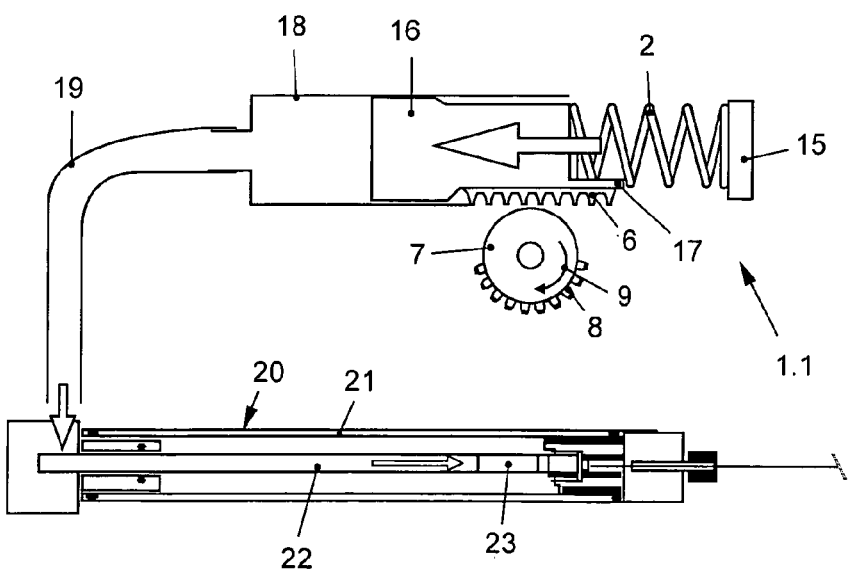

FIGS. 4 to 6 show a further exemplary embodiment of a shock wave generator 1.1 according to the invention. This has, similarly to the preceding exemplary embodiment, a spring member 2. This is introduced between an impact plate 15 and a piston 16. In order to guide the spring member 2, a rib 17 is integrally formed on the piston 16. The piston 16 is guided in a cylinder 18. Adjoining the latter is a flexible tube 19 in which a valve may be integrated if appropriate for better control or blocking. The flexible tube 19 is connected to a barrel 20. The barrel 20 comprises a housing 21 and a guide tube 22 for a projectile 23. At one end of the barrel 20 there is arranged a transmitting element 4.

The piston 16 and the rib 17 have, similarly to the preceding exemplary embodiment, a toothing formation 6. This is operatively connected to a pinion 7 which only partially has a toothed ring 8.

The present invention functions as follows:

Similarly to the above-described exemplary embodiment, the shock wave generator 1.1, too, is driven in the clockwise direction by an electric motor (not illustrated) via a reduction gear, the drive being symbolized by the arrow 9. In the process, the toothed ring 8 of the pinion 7 engages in the toothing formation 6, moves the piston 16 in the direction of the arrow 24 and presses the spring element 2 against the impact plate 15. In the process, the spring element 2 stores kinetic energy or impact energy. This is then suddenly, i.e. abruptly, released when the last tooth of the toothed ring 8 of the pinion 7 leaves the toothing formation 6. By way of this spring force, which is available on account of the brief release of tension in the compression spring 2, the piston 16 is then moved abruptly, as illustrated in FIG. 6, counter to the direction of the arrow 24 and presses the air located in the cylinder 18 and flexible tube 19 into the channel 22 in the barrel 20. As a result, the projectile 23 is shot onto the transmitting element 4. On account of the abrupt impact of the projectile 23 on the transmitting element 4, shock waves are produced in the latter, similarly to the above exemplary embodiment, and then may serve for the uses that have already been described.

Overall, the present invention provides a modular, cost-effective medical handheld appliance, which on account of its mechanical mode of operation is very robust and thus low-maintenance and can supply relatively high, precise impact energy and thus shock waves, which is of great advantage both for the user and for the respective patient.

The invention claimed is:

1. An apparatus for introducing shock waves into a living body, comprising:
    a transmitting element which transmits the shock waves into the living body;
    a percussion part for transmitting a shock pulse to the transmitting element, the percussion part having a toothing formation;
    a spring member for generating the shock pulse, wherein the spring member is operatively connected to the percussion part; and
    a tensioning device for abruptly triggering the spring member, the tensioning device comprising a pinion having an outer circumference, only a portion of the outer circumference having teeth which periodically engage the toothing formation for tensioning the spring member;
    wherein the spring member is triggered when the teeth on the outer circumference disengage from the toothing formation; and
    wherein spring force of the spring member, when the spring member is triggered, is transmitted as the shock pulse to the transmitting element by having the percussion part directly strike the transmitting element.

2. The apparatus as claimed in claim 1, wherein the percussion part is formed as a piston which is guided in a housing part and the piston has a head part that emits the shock pulses and a cylindrical hollow part that adjoins the head part.

3. The apparatus as claimed in claim 2, wherein the compression spring is guided at least partially in the cylindrical hollow part, wherein the compression spring is supported at one end on a rear side of the head part of the piston and at the other end on a housing part.

4. The apparatus as claimed in claim 3, wherein the cylindrical hollow part of the percussion part has along an outer casing the toothing formation or rack, into which the pinion or worm engages.

5. The apparatus as claimed in claim 3, wherein the piston has a rib as a guide for the spring member.

6. The apparatus as claimed in claim 2, wherein the piston has the toothing formation.

7. The apparatus as claimed in claim 1, including drive means for bringing the toothing formation into operative connection with the pinion.

8. The apparatus as claimed in claim 7, wherein the pinion has a partial toothed ring on a part of its circumference.

9. The apparatus as claimed in claim 8, wherein the partial toothed ring is provided over 180° of the circumference of the pinion.

10. The apparatus as claimed in claim 9, wherein the pinion is motor driven.

11. The apparatus as claimed in claim 10, wherein a drive for the pinion is configured as a battery-powered electric motor.

12. The apparatus as claimed in claim 1, including a triggerable retaining device provided for releasing the compression spring.

13. The apparatus as claimed in claim 1, wherein the transmitting element that transmits the shock pulse is arranged coaxially with respect to the percussion part.

14. The apparatus as claimed in claim 1, wherein the element is incorporated into an endoscope.

15. The apparatus as claimed in claim 14, wherein the element that transmits the shock pulse is designed as a rounded spherical segment for applying to a living body.

16. The apparatus as claimed in claim 15, wherein the apparatus is sized, as seen from its external dimensions, which allows the appliance to be held in an adult hand.

* * * * *